(12) United States Patent
Wong et al.

(10) Patent No.: US 9,285,308 B2
(45) Date of Patent: Mar. 15, 2016

(54) INTERFERENCE-COMPENSATING NDIR GAS SENSOR FOR MEASURING ACETYLENE

(71) Applicant: Wicor Holding AG, Rapperswil (CH)

(72) Inventors: Jacob Y Wong, Goleta, CA (US); Renyan Qin, London (CA); Daniel Tschudi, Rapperswil (CH)

(*) Notice: Subject to any disclaimer, the term of this patent is extended or adjusted under 35 U.S.C. 154(b) by 196 days.

(21) Appl. No.: 13/974,587

(22) Filed: Aug. 23, 2013

(65) Prior Publication Data

US 2015/0053861 A1    Feb. 26, 2015

(51) Int. Cl.
*G01N 21/3504* (2014.01)
*G01N 21/35* (2014.01)

(52) U.S. Cl.
CPC .................. *G01N 21/3504* (2013.01)

(58) Field of Classification Search
CPC ... G01N 21/3521; G01N 21/61; G01N 21/35; G01N 21/3504

USPC .......................................................... 250/343
See application file for complete search history.

(56) References Cited

U.S. PATENT DOCUMENTS

| 6,037,592 A * | 3/2000 | Sunshine et al. .............. 250/343 |
| 2007/0145275 A1* | 6/2007 | Wong ....................... 250/339.13 |
| 2012/0078532 A1* | 3/2012 | Forsyth et al. .................. 702/24 |

* cited by examiner

*Primary Examiner* — Mark R Gaworecki
(74) *Attorney, Agent, or Firm* — Roy L. Anderson

(57) ABSTRACT

A gas sample separated from transformer oil is circulated through an NDIR gas sensor system which obtains an acetylene concentration by calculating a detected acetylene concentration obtained by an absorption biased ("AB") NDIR acetylene gas sensor, calculating a detected carbon dioxide concentration obtained by an AB NDIR carbon dioxide gas sensor, calculating a detected water vapor concentration obtained by an AB NDIR water vapor NDIR gas sensor and then determining the acetylene concentration from the detected acetylene concentration through use of the detected carbon dioxide and water vapor concentrations to compensate for their interference.

4 Claims, 1 Drawing Sheet

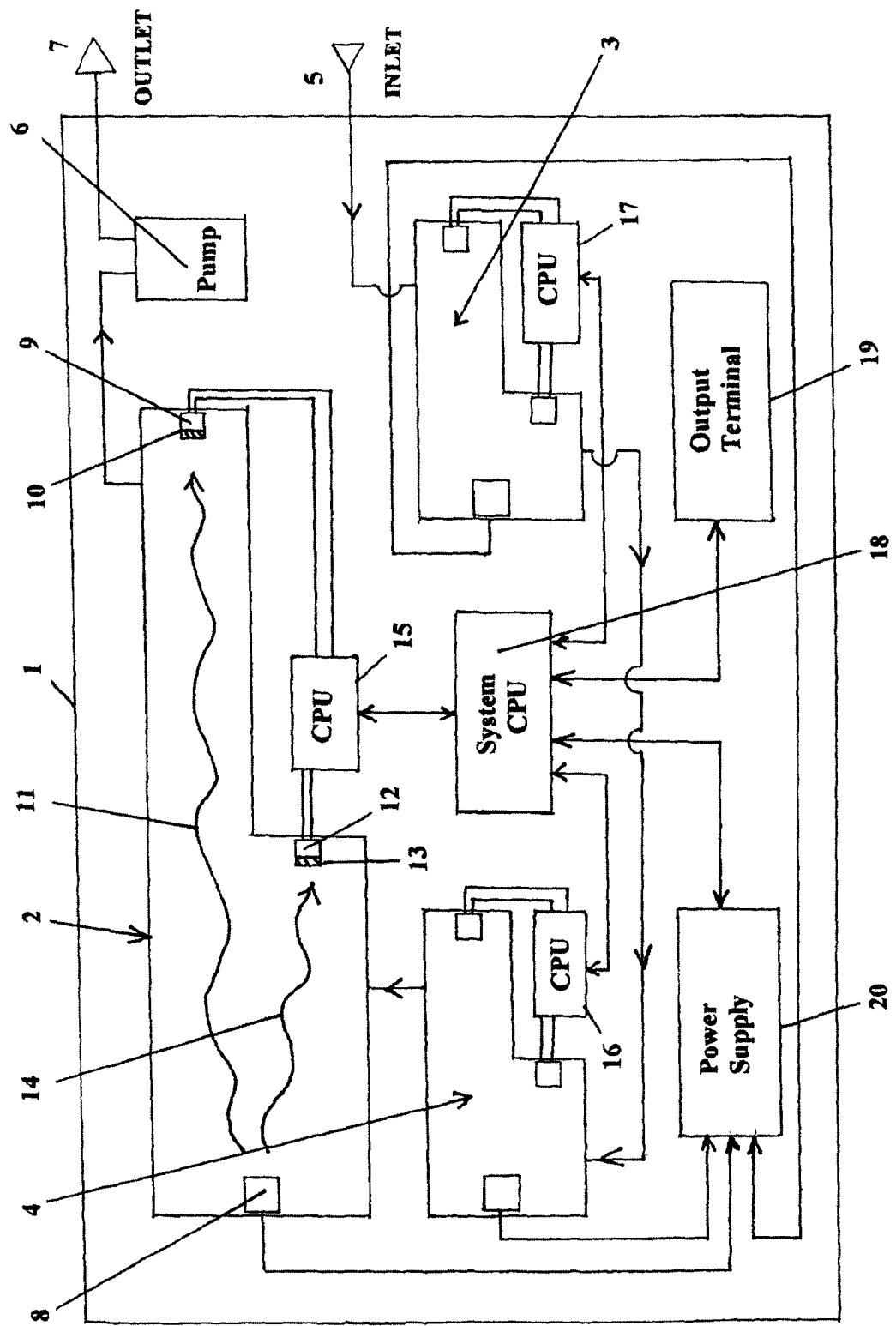

INTERFERENCE-COMPENSATING NDIR GAS SENSOR FOR MEASURING ACETYLENE

FIELD OF THE INVENTION

The present application is in the field of gas analysis, and specifically relates to a methodology employing a Non-Dispersive Infrared (NDIR) gas analysis technique to monitor gas samples obtained from a transformer oil so as to monitor for fault gases.

BACKGROUND OF THE INVENTION

Electrical transformers are known to degrade and fail due to aging, thermal and electrical stresses. When electrical transformers degrade and fail their insulation material—oil—breaks down and generates certain gases commonly referred to as "fault gases" which are dissolved in the degraded oil. Such fault gases may include hydrogen ($H_2$), carbon monoxide (CO), carbon dioxide ($CO_2$), methane ($CH_4$), acetylene ($C_2H_2$), ethylene ($C_2H_4$), and ethane ($C_2H_6$).

It is well known in the transformer industry that the amount and nature of fault gases can be used to identify the type and severity of the fault in the transformer. For example, hydrogen is often associated with low energy electrical discharge (corona) while acetylene is related to high energy arcing (*IEEE Std C57.104 —Guide for the Interpretation of Gases generated in oil-immersed transformers*).

Until now, utilities throughout the world have typically relied upon performing a dissolved gas analysis in a laboratory to check for fault gases, and this is typically only done once or twice a year. This practice may be effective for slow evolving faults, but it is not adequate to prevent fast evolving faults which often lead to catastrophic failure and significant damage to a transformer and other assets. And, in fact, there are many documented cases of critical transformer failures which have occurred catastrophically within days or even hours after being energized and/or after the onset of an increasing change in gas production.

Accordingly, there has been a long felt and significant need for a reliable and cost effective method and apparatus which is capable of continuously and quantitatively detecting and monitoring the concentration of key fault gases dissolved in insulating oil.

Although the ideal sensor system for measuring fault gases in transformer oil in order to avoid failure of transformers should detect all fault gases, and not just one or only a selected few, such an approach may not be practical when the total cost of purchasing and maintenance is taken into consideration. The detection of a very small amount but sudden increase of Acetylene ($C_2H_2$), in the hundreds of ppb levels or sub-ppm levels, has been considered by many experts in the field as one of the most reliable indications signaling the fact that a transformer has a degradation problem that can lead to transformer failure. Accordingly, designing a gas sensor system focusing on the detection of ppb or sub-ppm levels of acetylene should be a good compromise for detecting and monitoring transformer health in an asset management program.

SUMMARY OF THE INVENTION

The present invention is generally directed to a method in which a gas sample separated from transformer oil is circulated through an NDIR gas sensor system which obtains an acetylene concentration by calculating a detected acetylene concentration obtained by an absorption biased NDIR acetylene gas sensor, calculating a detected carbon dioxide concentration obtained by an absorption biased NDIR carbon dioxide gas sensor, calculating a detected water vapor concentration obtained by an absorption biased NDIR water vapor NDIR gas sensor and then determining the acetylene concentration from the detected acetylene concentration through use of the detected carbon dioxide and water vapor concentrations to compensate for their interference.

The absorption biased NDIR acetylene gas sensor can use a thermopile detector with an average D* around $1\times10^8$ cm $Hz^{0.5}$ $W^{-1}$ while the FWHM of its narrow band pass filter does not exceed 0.1µ, have a path length of approximately twenty inches or more and utilize a MEMS infrared source with built-in collimating optics.

Accordingly, it is a primary object of the present invention to advance an NDIR gas sensor system that can be used to detect and monitor acetylene in gas samples obtained from electrical transformer oil to detect its early degradation and thus prevent critical failures of electrical transformers.

This and further objectives and advantages will be apparent to those skilled in the art in connection with the drawings and the detailed description of the invention set forth below.

BRIEF DESCRIPTION OF THE DRAWINGS

FIG. 1 depicts the component layout for an acetylene sensor system according to the present invention.

DETAILED DESCRIPTION OF THE INVENTION

The present invention advances a methodology for the design of an NDIR gas sensor system which is capable of detecting sub-ppm levels of Acetylene gas in transformer oil in the presence of multiple fault gases and moisture. In order to achieve a successful methodology, a number of technical obstacles must be recognized, addressed and overcome.

The present invention addresses the drawback of NDIR gas sensors for detecting gases in the sub-ppm concentration ranges having very weak absorption bands located in the far infrared region of the electromagnetic spectrum (>12.0µ) and very unique ultra-narrow line shapes and overcomes these drawbacks by a novel NDIR design methodology. This design methodology comprises 1) matching the ultra-narrow line shape of the gas' absorption band with a carefully designed narrow band pass filter; 2) making sure that the out-of-band leakage of the filter is not more than one part in $10^3$; 3) utilizing a MEMS infrared source with built-in collimating optics and a large area thermopile detector for S/N optimization; 4) using a sufficiently long path length waveguide sample chamber for achieving adequate modulation by the target gas and 5) including a sensitive $CO_2$ and a sensitive Dew Point NDIR sensor for simultaneously measuring the concentration levels of both gases in order to compensate for any possible interferences by these gases to the measurement of the target gas.

The first step needed to advance a successful methodology is to design a narrow infrared band pass filter with a center wavelength (CWL) specified at 13.70µ coincident with the center wavelength of the absorption line of Acetylene and with an adequately narrow full width at half-maximum (FWHM). The FWHM of the specified narrow band pass filter must be narrow enough so as to afford adequate signal modulation for measuring concentration levels down to sub-ppm or ppb for Acetylene gas. In order to be able to detect Acetylene down to +/−0.5 ppm concentration level, a thermopile detector is used with an average D* around $1 \times 10^8$ cm $Hz^{0.5}$ $W^{-1}$ and the FWHM of the narrow band pass filter must not exceed $0.1\mu$.

With the required spectral properties for the narrow band pass filter determined, step two is to calculate the path length for the sample chamber required to be able to accurately measure concentration levels of Acetylene down to +/−0.5 ppm. Calculations showed that based upon the very weak absorption of Acetylene gas, the minimum path length required to get the job done is no less than ~20 inches.

The third step is to recognize the possibility of interference effects on the measurement accuracy for Acetylene by other gases and then compensate for any such interference. After a careful study it was found that only two gases, namely carbon dioxide ($CO_2$) and water vapor ($H_2O$), could severely interfere with the measurement accuracy of Acetylene at $13.70\mu$. For $CO_2$, it is due to the presence of a very strong absorption band at $~15.0\mu$. Water vapor on the other hand has absorption bands almost everywhere in the infrared extending way into the far infrared wavelength region. Even though water vapor has several very strong absorption bands in the infrared, those that are present around $13.70\mu$ are extremely weak. Due to the fact that the FWHM of the specified filter is only $~0.1\mu$, it is not expected that water vapor will cause any interference problem. However, the state-of-the-art for making a narrow band pass interference filter in the far infrared today only guarantees spectral blocking outside of the designed pass band to be no better than $1:10^3$. Thus, because of the omnipresence of water vapor absorption lines everywhere, the out-of-the-band absorption, i.e. for the wavelength region outside of the FWHM at $13.70\mu$, the interference effect of water vapor is still very significant. Furthermore, because of the fact that the amount of water vapor present in air or dissolved in the transformer oil could vary from a few to tens of mmHg (1 mmHg=1,316 ppm at Standard Temperature and Pressure [STP] conditions), its interference effects on the measurement accuracy of Acetylene cannot be ignored. In conclusion, after a careful analysis of the subject, the interference effects of both $CO_2$ and water vapor must be carefully taken into consideration before the measurement accuracy of Acetylene down to sub-ppm levels can be confidently realized.

To take the interference effects of both $CO_2$ and water vapor on the measurement accuracy of Acetylene into consideration is in theory not a complicated task. One practical and viable approach is to first ascertain quantitatively, based upon the narrow band pass filter to be used in the design of the Acetylene sensor, the amount of Acetylene that is equivalent to a certain known amounts of both $CO_2$ and water vapor. The experimentally measured results indicated that under the same measurement conditions, the presence of 5,000 ppm of $CO_2$ would be equivalent to the presence of 20 ppm of Acetylene and the presence of 8.0 mmHg of water vapor ($H_2O$) would be equivalent to 40 ppm of Acetylene. Thus, in order to be able to guarantee the accuracy of +/−0.5 ppm of Acetylene, one must be able to accurately detect +/−5,000/40 or +/−125 ppm of $CO_2$ and +/−8.0/80 mmHg or +/−0.1 mmHg of water vapor simultaneously while measuring Acetylene using the same sensor in order to adequately compensate for their presence as interfering gases.

As it turns out, it is possible to design an output stable NDIR $CO_2$ gas sensor capable of detecting the gas with an accuracy of +/−100 ppm and with a reasonable response time (0-90%) commensurate with that required for measuring Acetylene which is 3-5 minutes. The challenge lies in the fact that an output stable NDIR dew point or water vapor sensor capable of detecting the gas with an accuracy of +/−0.1 mmHg simply cannot be found anywhere today. Using a conventional humidity sensor and converting its output to water vapor pressure by measuring also the temperature will not work because of two factors. First, humidity sensors are known to have output drifts that are difficult to determine over time. Second, presently available humidity sensors are not accurate enough to meet the required accuracy of +/−0.1 mmHg. Thus, the present invention has to embark on an additional innovative step to realize an NDIR gas sensor capable of measuring water vapor pressure with an accuracy of +/−0.1 mmHg and a response time (0-90%) of 3-5 minutes.

Finally in order to complete a well-thought-out measurement methodology, the best available infrared source and thermopile detector must be selected for the design of the sensor. At the same time the accompanying signal processing electronic system should also be designed to be detector-noise-limited. In other words, the overall noise of the sensor can only be limited by the detector and not by the infrared source, the electronic signal processing circuit or any part of the remaining system.

FIG. 1 depicts the component layout for $C_2H_2$ sensor system 1 according to the present invention which incorporates the design methodology described and explained earlier. As shown in the schematic, sensors 2, 3 and 4 are respectively for the detection of $C_2H_2$, $CO_2$ and $H_2O$. A gas sample is drawn through inlet 5 through the $CO_2$ sensor 3, the $H_2O$ sensor 4 and then the $C_2H_2$ sensor 2 by a pump 6 before exiting the sensor system 1 at outlet 7. In this way, the amounts of $H_2O$, $CO_2$ and $C_2H_2$ can be simultaneously measured. The concentration levels of $H_2O$ and $CO_2$ will be used to compensate for the measurement of $C_2H_2$ due to their presence in the gas sample because of their interference effects.

Gas sensor 2 in FIG. 1 is an Absorption Biased (AB) designed $C_2H_2$ NDIR gas sensor. AB designed NDIR gas sensors and their methodology are explained in U.S. Pat. No. 8,143,581, the disclosure of which is specifically incorporated herein by reference. An AB designed NDIR gas sensor creates an absorption bias between signal and reference outputs which are used to determine a sample concentration of a gas being measured and the absorption bias is created by using a signal channel with a path length that is greater than a path length of a reference channel in the sample chamber while both the signal and reference detectors have an identical narrow band pass filter with the same Center Wavelength ("CWL"), Full Width Half Maximum (FWHM) and transmittance efficiency at the CWL.

Gas sensor 2 has a Micro-Electro-Mechanical-Systems (MEMS) infrared source 8 operating nominally at 450° C. sending radiation to a thermopile detector 9 equipped a narrow pass band filter 10 with CWL=$13.70\mu$ and a very narrow FWHM=$0.1\mu$ through a longer sample path 11 (typically ~16"). The same MEMS source 8 also sends radiation to another thermopile detector 12 equipped with filter 13 having identical characteristics as filter 10 through a shorter sample path 14 (typically ~6.0"). The MEMS source 8 and detector 9 together with the longer sample path 11 constitutes the Signal Beam and the MEMS source 8 and detector 12 together with the shorter sample path 14 constitutes the Reference Beam of the AB designed NDIR $C_2H_2$ gas sensor 2.

Sensors 3 and 4 as shown in FIG. 1 for the detection of $CO_2$ and $H_2O$ respectively with a minimum accuracy of +/−100 ppm and +/−0.1 mmHg, are also AB designed NDIR gas sensors. All the sensors in sensor system 1 have their own individual signal processing CPUs, respectively 15, 16 and 17, all connected to the same CPU 18 of the system sensor 1. The measurement data generated by sensors 2, 3 and 4, respectively for the concentration levels of $CO_2$, $H_2O$ and C₂H₂ are all communicated to CPU 18 of the sensor system 1 for analysis and interference compensation before they are sent to terminal 19 of sensor system 1 for output. The power supply 20 of sensor system 1 also provides power for driving the infrared sources and electronics for all the three onboard gas sensors.

Accordingly, sensor system 1 of the present invention can be used to help identify the type and severity of faults in electrical transformers. This is done by obtaining a gas sample separated from a transformer oil, circulating the gas sample through system sensor 1 and then obtaining an acetylene concentration from the gas sample (accurate to 1.0 ppm) in accordance with the above teachings. Because the acetylene concentration can be monitored on an essentially continuous basis, if desired, such a system and methodology offers great advantages and cost savings over the best current practices of the transformer industry and can help prevent critical failures of electrical transformers by early recognition of the breakdown of transformer oil.

While the invention has been described herein with reference to a preferred embodiment, this embodiment has been presented by way of example only, and not to limit the scope of the invention. Additional embodiments thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions.

What is claimed is:

1. A method, comprising the steps of:
    obtaining a gas sample separated from a transformer oil;
    circulating the gas sample through a non-dispersive infrared ("NDIR") gas sensor system; and
    obtaining an acetylene concentration of the gas sample by the following steps:
        calculating a detected acetylene concentration obtained by an absorption biased NDIR acetylene gas sensor of the NDIR gas sensor system comprised of a thermopile detector with an average detectivity around $1 \times 10^8$ cm $Hz^{0.5}$ $W^{-1}$ and a Full-Width Half Maximum of a narrow band pass filter used in the thermopile detector does not exceed 0.1μ;
        calculating a detected carbon dioxide concentration obtained by an absorption biased NDIR carbon dioxide gas sensor of the NDIR gas sensor system;
        calculating a detected water vapor concentration obtained by an absorption biased NDIR water vapor NDIR gas sensor of the NDIR gas sensor system; and
        using the detected carbon dioxide concentration and the detected water vapor concentration to compensate for interference of carbon dioxide and water vapor present in the gas sample to determine the acetylene concentration from the detected acetylene concentration.

2. A non-dispersive infrared ("NDIR") gas sensor system for detecting an acetylene concentration of a gas sample obtained from a transformer oil, comprising:
    an absorption biased NDIR acetylene gas sensor for calculating a detected acetylene concentration;
    an absorption biased NDIR carbon dioxide gas sensor for calculating a detected carbon dioxide concentration;
    an absorption biased NDIR water vapor gas sensor calculating a detected water vapor concentration obtained by; and
    and electronics for using the detected carbon dioxide concentration and the detected water vapor concentration to compensate for interference of carbon dioxide and water vapor present in the gas sample to determine the acetylene concentration from the detected acetylene concentration;
    wherein the absorption biased NDIR acetylene gas sensor is further comprised of a thermopile detector with an average detectivity around $1 \times 10^8$ cm $Hz^{0.5}$ $W^{-1}$ and a Full-Width Half Maximum of a narrow band pass filter used in the thermopile detector does not exceed 0.1μ.

3. The NDIR gas sensor system of claim 2 wherein the absorption biased NDIR acetylene gas sensor has a path length of approximately twenty inches or more.

4. The NDIR gas sensor system of claim 3 wherein the absorption biased NDIR acetylene gas sensor utilizes a MEMS infrared source with built-in collimating optics.

* * * * *